United States Patent
Tang et al.

(10) Patent No.: US 8,268,160 B2
(45) Date of Patent: Sep. 18, 2012

(54) CORROSION TESTING OF FUEL-CELL SEPARATOR PLATE MATERIALS

(75) Inventors: Jason M. Tang, Hillsboro, OR (US); Yang Song, Portland, OR (US)

(73) Assignee: ClearEdge Power, Inc., Hillsboro, OR (US)

( * ) Notice: Subject to any disclaimer, the term of this patent is extended or adjusted under 35 U.S.C. 154(b) by 335 days.

(21) Appl. No.: 12/612,574

(22) Filed: Nov. 4, 2009

(65) Prior Publication Data

US 2011/0100841 A1    May 5, 2011

(51) Int. Cl.
*G01N 17/00* (2006.01)
(52) U.S. Cl. ............................ 205/775.5; 429/516
(58) Field of Classification Search .......... 205/775–777; 204/404; 429/1–535
See application file for complete search history.

(56) References Cited

U.S. PATENT DOCUMENTS

| | | | |
|---|---|---|---|
| 4,049,525 A | 9/1977 | Dutton et al. | |
| 5,407,555 A * | 4/1995 | Winsel | 204/435 |
| 6,083,641 A * | 7/2000 | LaConti et al. | 429/210 |
| 6,454,922 B1 | 9/2002 | Weisbrod | |

* cited by examiner

*Primary Examiner* — J. Christopher Ball
(74) *Attorney, Agent, or Firm* — Alleman Hall McCoy Russell & Tuttle LLP (57) ABSTRACT

In one example, a specimen is immersed in an electrolyte, and a plurality of potentials of the specimen are experimentally related to a plurality of currents by applying the potentials to the specimen while measuring the currents, or, by drawing the currents through the specimen while measuring the potentials. The potentials are referenced to a hydrogen reference electrode. Hydrogen is supplied to the hydrogen reference electrode via an electrolysis cathode distinct from the hydrogen reference electrode. In another example, an electrochemical cell confines a head gas disposed over the electrolyte. A partial pressure of water vapor in the head gas is adjusted so that the concentration of water in the electrolyte, when equilibrated with the head gas, falls within a predetermined concentration range. The head gas and electrolyte are then equilibrated, thereby controlling the concentration of water in the electrolyte, and an electrochemical property of the specimen is measured.

17 Claims, 5 Drawing Sheets

CORROSION TESTING OF FUEL-CELL SEPARATOR PLATE MATERIALS

TECHNICAL FIELD

The present application relates to the field of electrochemical materials testing, and more particularly, to characterizing the corrosion properties of separator plate materials used in high-temperature polymer-electrolyte membrane and phosphoric acid fuel cells.

BACKGROUND

A fuel cell may include a solid, liquid, or gel-like electrolyte that separates a catalyzed anode from a catalyzed cathode. The catalyzed anode may support electrochemical oxidation of a fuel, such as hydrogen or methanol, and the catalyzed cathode may support electrochemical reduction of oxygen. As these reactions occur, electric current flows from the cathode to the anode, via an external circuit.

Accordingly, the fuel cell may include two separator plates—a first separator plate disposed in contact with the catalyzed anode, and a second separator plate disposed in contact with the catalyzed cathode. Each separator plate may conduct electric current to or from its respective electrode and may further constrain the flow of electrode gases (reaction products, fuel, or air) along a prescribed flow path. It is generally desired that the separator plates of a fuel cell be resistant to corrosion, particularly within the working fuel cell. However, achieving adequate corrosion resistance for separator plate materials may require effort and experimentation, as some constituents of the fuel cell—notably the electrolyte—may be highly corrosive. For instance, some fuel cells include concentrated phosphoric acid as an electrolyte; some others include a polymer-electrolyte membrane in which phosphoric acid is sorbed.

The process of developing a durable fuel cell may therefore include a materials-testing phase, where candidate separator plate materials are characterized for corrosion resistance in environments comparable to that of a working fuel cell. One such test procedure comprises constructing a prototype fuel cell, complete with catalyzed electrodes and separator plates formed from candidate materials, and conducting long-term durability testing of the prototype. However, the inventors herein have noted that this approach may be time-consuming, labor-intensive, and therefore inapplicable to the rapid screening of novel separator plate materials.

SUMMARY

Therefore, one embodiment provides a method for conducting a corrosion test on a specimen. The specimen is immersed in an electrolyte confined within an electrochemical cell. The method comprises experimentally relating a plurality of potentials of the specimen to a plurality of currents drawn through the specimen by applying the plurality of potentials to the specimen while measuring the plurality of currents, or, by drawing the plurality of currents through the specimen while measuring the plurality of potentials. In this method, the plurality of potentials are referenced to a hydrogen reference electrode also immersed in the electrolyte. The method further comprises supplying hydrogen to the hydrogen reference electrode via an electrolysis cathode distinct from the hydrogen reference electrode.

Another embodiment provides a related method for conducting a corrosion test on a specimen, where the specimen is again immersed in an electrolyte confined within an electrochemical cell. Here, the electrochemical cell also confines a head gas disposed over the electrolyte. The method comprises adjusting a partial pressure of water vapor in the head gas so that the concentration of water in the electrolyte, when equilibrated with the head gas, will fall within a predetermined concentration range. The method further comprises equilibrating the head gas with electrolyte, thereby controlling the concentration of water in the electrolyte, and then measuring an electrochemical property of the specimen.

It will be understood that the summary above is provided to introduce in simplified form a selection of concepts that are further described in the detailed description, which follows. It is not meant to identify key or essential features of the claimed subject matter, the scope of which is defined by the claims that follow the detailed description. Further, the claimed subject matter is not limited to implementations that solve any disadvantages noted above or in any part of this disclosure.

BRIEF DESCRIPTION OF THE DRAWINGS

The subject matter of the present disclosure will be better understood from reading the following detailed description of non-limiting embodiments, with reference to the attached drawings, wherein.

DETAILED DESCRIPTION

The subject matter of the present disclosure is now described by way of example and with reference to certain illustrated embodiments. Components that may be substantially the same in one or more embodiments are identified coordinately and are described with minimal repetition. It will be noted, however, that components identified coordinately may be at least partly different. It will be further noted that the drawings included in this disclosure are schematic. Views of the illustrated embodiments are generally not drawn to scale; aspect ratios, feature size, and numbers of features may be purposely distorted to make selected features or relationships easier to see.

Figure 1:
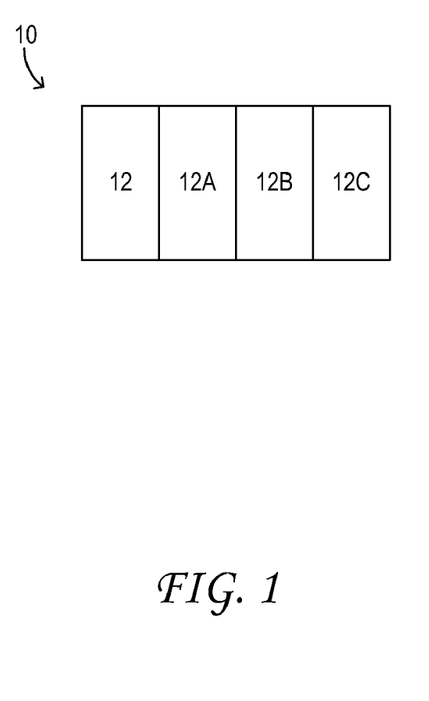
FIG. 1 schematically shows a fuel-cell stack in accordance with an embodiment of the present disclosure.

FIG. 1 schematically shows fuel-cell stack 10 in one example embodiment. The fuel cell stack may be configured to admit fuel and air to a plurality of fuel cells included therein, and to generate an electric current via electrochemical oxidation of the fuel by oxygen from the air. The fuel may be hydrogen or methanol, for example. In some embodiments, the fuel and air may be distributed within the fuel-cell stack via internal or external fuel and air manifolds (not shown in the drawings).

Figure 2:
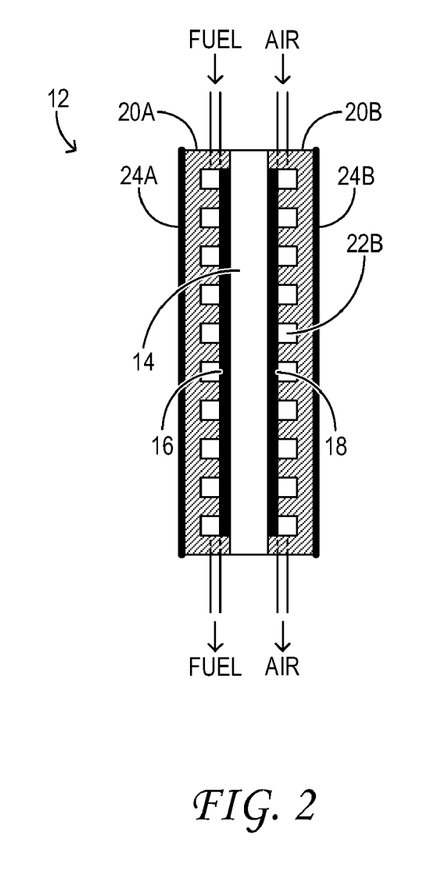
FIG. 2 schematically shows a fuel cell in accordance with an embodiment of the present disclosure.

In the embodiment illustrated in FIG. 1, fuel-cell stack 10 includes fuel cells 12, 12A, 12B, and 12C, arranged in series for combined voltage output. Each of the fuel cells may be substantially the same, or at least partly different. FIG. 2 schematically shows fuel cell 12 in greater detail, in one example embodiment.

Fuel cell 12 is a polymer-electrolyte membrane (PEM) fuel cell. It comprises PEM 14, which may be any suitable PEM configured to conduct protons, hydronium ions, or the equivalent. Proton conduction through the PEM may take place via ionized pendant moieties arranged on a cross-linked polymer phase within the PEM. In some embodiments, the PEM may comprise a sorbed liquid phase containing an ionizable liquid and/or an ionized solute. In such embodiments, at least some proton conduction through the PEM may take place via ionized species within the sorbed liquid phase. In one embodiment, the sorbed liquid may comprise phosphoric acid.

Fuel cell 12 includes two catalyzed electrodes, viz., catalyzed anode 16 and catalyzed cathode 18. The catalyzed electrodes may be formed from carbon cloth or carbon fiber paper, for example. The catalyzed electrodes may further comprise catalysts, which accelerate the electrochemical oxidation of the fuel and/or reduction of oxygen. In fuel cell 12, the catalyzed electrodes are each sandwiched between PEM 14 and one of two separator plates. Accordingly, FIG. 2 shows anodic separator plate 20A and cathodic separator plate 20B. The separator plates provide structural support for the PEM and the catalyzed electrodes, conduct current to and from the catalyzed electrodes, and confine the fuel flow and the air flow in the fuel cell to predefined flow paths, e.g., flow path 22B. Each separator plate may be formed from graphite, from a metal, or from a composite material containing graphite and a suitable binder, for example. The material or materials from which the separator plates are formed may be chosen based inter alia on resistance to corrosion within the fuel-cell environment. For example, if PEM 14 comprise phosphoric acid, the separator plates may be formed from a material shown to resist corrosion in phosphoric-acid media over the range of potentials experienced by the separator plates in a working fuel cell.

Continuing in FIG. 2, fuel cell 12 further includes anodic current collector 24A and cathodic current collector 24B. Each current collector may be a metallic screen or foil, for example, configured to pass current from its respective separator plate to an external circuit or to an adjacent fuel cell in fuel cell stack 10.

Although FIG. 2 illustrates a PEM fuel cell, it will be understood that other, quite different fuel-cell variants are fully consistent with the present disclosure. For example, in a non-PEM fuel cell having liquid phosphoric acid as the electrolyte, catalyzed electrodes may be supported by separator plates, whose corrosion resistance is relevant to the performance and longevity of the fuel cell.

Figure 3:
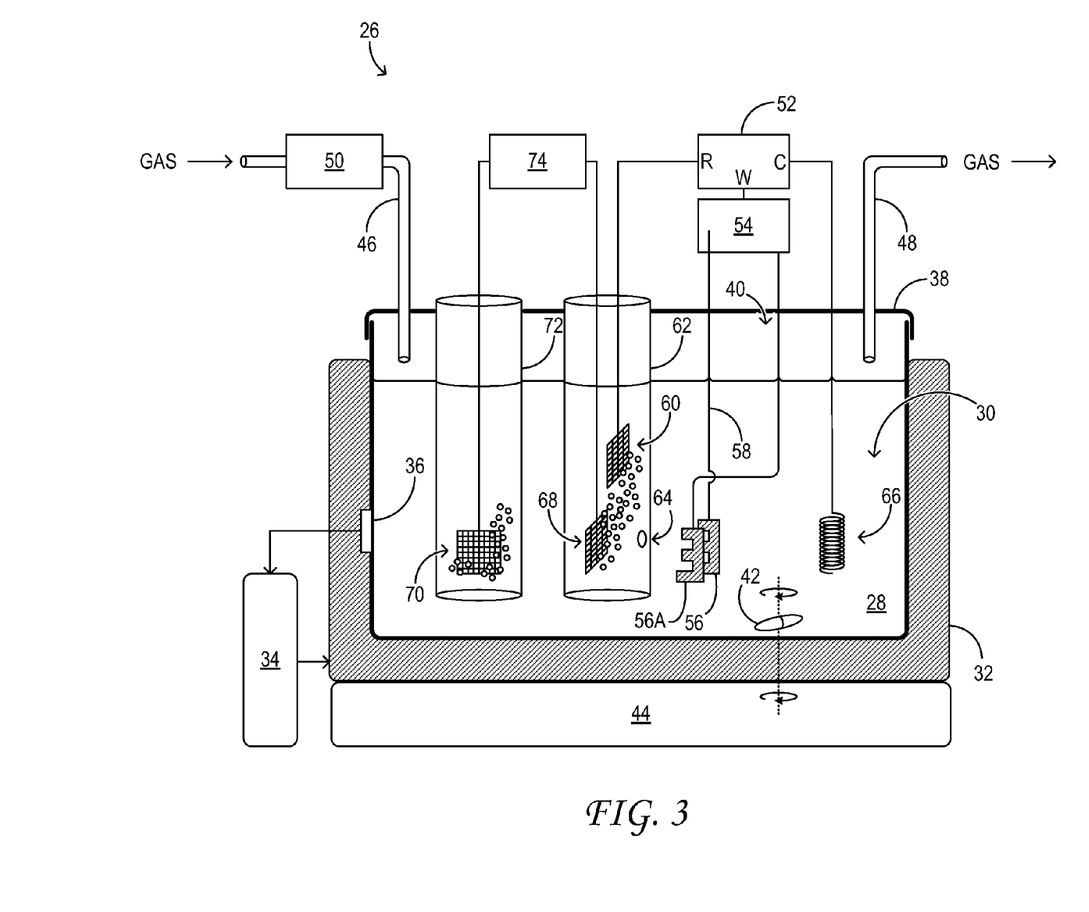
FIG. 3 schematically illustrates a corrosion-test system for testing the corrosion properties of one or more specimens in accordance with an embodiment of the present disclosure.

Accordingly, FIG. 3 schematically illustrates an example corrosion-test system 26 for testing the corrosion properties of one or more specimens. The corrosion-test system may be used to measure the corrosion properties of candidate separator plate materials, for example. Corrosion-test system 26 includes electrochemical cell 28, which is charged with electrolyte 30. The electrolyte may comprise some or all of the electrolyte constituents of the fuel cell in which the one or more specimens are intended to be used. In one embodiment, the electrolyte may comprise concentrated, aqueous or anhydrous phosphoric acid (85 to 103% $H_3PO_4$, for example). Naturally, the electrochemical cell may be formed from one or more materials resistant to corrosion by the electrolyte over the range of temperatures used during a corrosion test. In embodiments where the electrolyte comprises concentrated, aqueous phosphoric acid, the electrochemical cell may be formed from polytetrafluoroethylene (PTFE). An electrochemical cell formed from PFTE may be used with phosphoric-acid electrolytes at temperatures as high as 250° C. The use of other acid resistant polymer materials—high-density polyethylene (HDPE), for example—may provide adequate stability over a narrower temperature range. These same corrosion-resistant materials may be used in various other components of the corrosion-test system that may be exposed to a corrosive electrolyte.

In the embodiment illustrated in FIG. 3, the electrochemical cell is enclosed by heating jacket 32. The heating jacket may comprise a resistive heating wire configured to provide heat to the electrochemical cell, and an insulating blanket configured to hinder the loss of heat from the electrochemical cell to the ambient. In the illustrated embodiment, the heating jacket is powered and controlled by temperature controller 34. The temperature controller may be any suitable device configured to maintain electrolyte 30 at one or more predetermined, set-point temperatures. To this end, the temperature controller may be operatively coupled to temperature sensor 36, which may be any suitable thermocouple or temperature-sensitive semiconductor device. In the illustrated embodiment, the temperature sensor is mounted on and exterior the electrochemical cell, and confined between the electrochemical cell and the heating jacket. In other embodiments, however, the temperature sensor may be mounted in a protective well, which is immersed in the electrolyte. In still other embodiments, the temperature sensor may be an infrared detector device mounted external and within a suitable range of the electrochemical cell.

In some embodiments fully consistent with this disclosure, heat may be supplied to electrochemical cell 28 via a heat exchanging fluid instead of a resistive wire. In such embodiments, the flow of the heat-exchanging fluid may be controlled via a temperature controller operatively coupled to a temperature sensor. Further, the heat-exchanging fluid may, in some embodiments, provide cooling as well as heating, so as to maintain electrolyte 30 at one or more predetermined set-point temperatures.

Continuing in FIG. 3, electrochemical cell 28 is fitted with and covered by a cell cover 38, which encloses head gas 40. In other words, the head gas is confined between the cell cover and the surface of electrolyte 30. The cell cover is coupled to gas inlet 46, through which a gas—argon, nitrogen, carbon dioxide, or air, for example—flows over or through the electrolyte. The cell cover also includes gas outlet 48, through which the head gas flows out into the ambient or gas-handling system. Confinement of the head gas and the electrolyte in the same vessel allows volatile components of the electrolyte to reach equilibrium with the head gas. Such equilibrium provides that the concentrations of the volatile components may be controlled indirectly, by controlling the partial pressures of the corresponding components of the head gas. For example, if the electrolyte comprise a relatively small concentration of water dissolved in phosphoric acid, the concentration of the water—and, therefore, the concentration of phosphoric acid, and, the hydrogen-ion activity in the electrolyte—may be controlled by controlling the partial pressure of water vapor in the head gas. Equilibrium between the head gas and the electrolyte may be ensured by maintaining the head gas above the electrolyte for a predetermined period of time between successive electrochemical measurements. In some embodiments, the rate of equilibration may be accelerated by temporarily allowing the gas from gas inlet 46 to bubble through the electrolyte. In still other embodiments, the rate of equilibration may be accelerated by temporarily stirring the electrolyte. Accordingly, FIG. 3 shows magnetic stir bar 42 magnetically coupled to stirring motor 44. In general, stirring and/or bubbling through gas inlet 46 may be discontinued while acquiring electrochemical data and resumed thereafter.

To control the water-vapor content in head gas 40, humidifier/dehumidifier 50 is coupled to gas inlet 46. The humidifier/dehumidifier may be any device configured to control the partial pressure of water vapor in the gas flowing to the gas inlet. In one, non-limiting embodiment, the humidifier/dehumidifier may be a temperature-controlled bubbler or impinger charged with water and configured to saturate the gas with water vapor. In this manner, the concentration of water in the electrolyte may be adjusted as need for any desired corrosion test.

FIG. 3 shows analyzer 52 configured to measure a corrosion property of one or more specimens mounted in electrochemical cell 28. The analyzer may be any electronic device configured to apply a suitable bias among the various electrodes and specimens of corrosion-test system 26, and to measure the appropriate voltages and/or currents among the electrodes, so as to enact an electrochemical test. In some embodiments, the analyzer may comprise a potentiostat operatively coupled to a waveform generator and interfaced to a computer. Accordingly, FIG. 3 shows three terminals of the analyzer, labeled R, W, and C, and corresponding, respectively, to the reference-electrode, working-electrode, and counter-electrode terminals of a potentiostat. To enable the analysis of multiple specimens during a single test, the analyzer in FIG. 3 is operatively coupled to multiplexer 54. The multiplexer may comprise an electronically controllable switch configured to link the working-electrode terminal of the potentiostat to any one of a series of specimens, which are held at the same distance from the hydrogen reference electrode 60 to equalize solution resistance for easier interpretation of results. Accordingly, FIG. 3 shows specimen 56 and specimen 56A both coupled to the multiplexer. Other embodiments may include additional specimens, each connected to a different terminal of the multiplexer. Still other embodiments may include only one specimen. Each specimen is coupled to the multiplexer via a substantially non-redox-active connector, such as connector 58. The connector may comprise a wire—e.g., a platinum wire. In one embodiment, the connector may be coupled to the specimen via a substantially non-redox-active fastener, such as a PTFE machine screw.

In the embodiment shown in FIG. 3, the reference-electrode terminal of the analyzer is coupled to hydrogen reference electrode 60. The hydrogen reference electrode may comprise a platinized platinum mesh. It will be understood that 'platinized platinum' is a term of art used to describe a article formed from platinum and additionally comprising at least a partial coating of electrochemically deposited platinum black. Continuing in FIG. 3, the hydrogen reference electrode is partly enclosed in hydrogen-segregating tube 62, which partly encloses the hydrogen reference electrode and partly separates the electrolyte nearest the hydrogen reference electrode from the balance of the electrolyte.

As further shown in FIG. 3, hydrogen-segregating tube 62 includes a passage 64—e.g., a hole—through which the electrolyte inside the hydrogen-segregating tube communicates with the electrolyte outside the hydrogen-segregating tube. In particular, the passage may be disposed relatively close to the specimen to minimize the ohmic potential drop resulting from ionic current flowing through the uncompensated solution resistance of the electrolyte. In other embodiments, the hydrogen-segregating tube may comprise virtually any region of increased porosity or permeability disposed between the hydrogen reference electrode and the specimen.

In the embodiment shown in FIG. 3, the counter-electrode terminal of analyzer 52 is coupled to a coiled length of platinum wire 66, also immersed in electrolyte 30. In other embodiments, the counter-electrode terminal of the analyzer may be coupled to the reference-electrode terminal of the analyzer, and the coiled platinum wire omitted from the configuration.

In the embodiment shown in FIG. 3, the zone of electrolyte 30 inside hydrogen-segregating tube 62 is supplied hydrogen via electrolysis cathode 68, which is also suspended within the hydrogen-segregating tube. The electrolysis cathode may be a platinized platinum mesh, for example. The hydrogen supplied via the electrolysis cathode is derived from the electrolysis of water in the electrolyte, which further involves the evolution of oxygen at electrolysis anode 70. In the embodiment illustrated in FIG. 3, the electrolysis anode is partly enclosed in oxygen-segregating tube 72, which partly separates the electrolyte nearest the electrolysis anode from the balance of the electrolyte to limit the diffusion of oxygen throughout electrolyte. In the embodiment illustrated in FIG. 3, the electrolysis anode and the electrolysis cathode are biased against each other via power supply 74, which may be any adjustable controlled-current or controlled-voltage power supply.

Continuing in FIG. 3, hydrogen-segregating tube 62 defines a zone of electrolyte 30 in which hydrogen reference electrode 60 is immersed; this zone is continuously sparged with and saturated with hydrogen. Further, the gas above the zone, effectively separated from head gas 40 by the hydrogen-segregating tube, comprises hydrogen at approximately 1 atm. As noted above, the hydrogen-ion activity in the electrolyte can be controlled by controlling the partial pressure of water vapor in head gas 40. Therefore, inasmuch as the partial pressure of hydrogen above the electrolyte is effectively constant, it follows that the hydrogen reference electrode will have a stable Nernst potential under conditions of zero load.

In this respect, hydrogen reference electrode 60 may be similar in function to a commercially available reversible hydrogen electrode (RHE), but unlike the RHE, hydrogen reference electrode 60 is made from materials particularly resistant to concentrated phosphoric acid—such as PTFE, HDPE, and the like—and requires no external source of hydrogen, such a high-purity, compressed hydrogen cylinder. It will be noted that some existing approaches to supplying hydrogen for an RHE have involved uniting the RHE with a electrolysis cathode, which is biased against an electrolysis anode. This type of reference is sometimes called a dynamic hydrogen electrode (DHE). However, the inventors herein find that the configurations described herein improve upon the DHE by providing a reference signal more reliable in at least three respects: first, the reference signal is less prone to noise due to gas-bubble convection; second, the reference signal is less prone to dissolved-oxygen leakage from the electrolysis anode; and third, the reference signal is less prone to the effects of concentration polarization caused by the electrolysis current.

Figure 4:
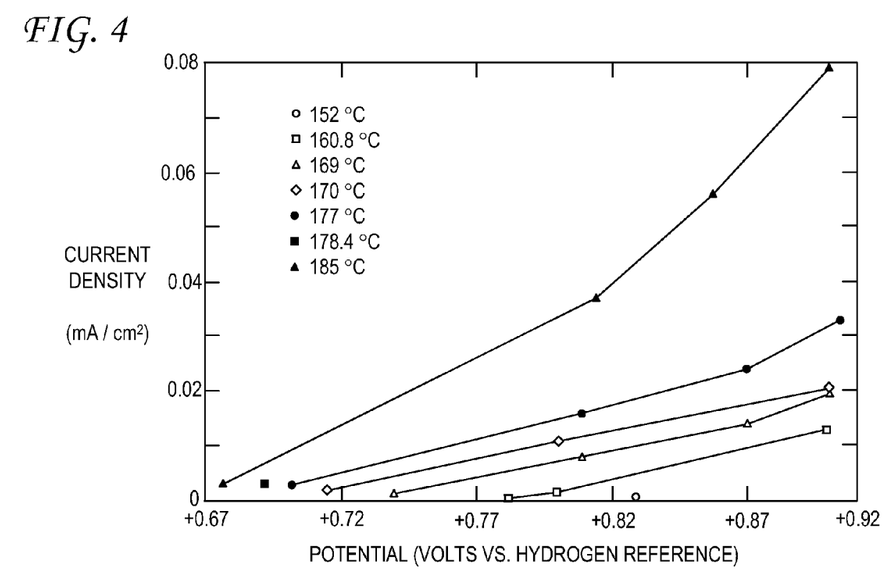
FIGS. 4-6 show graphs illustrating example results of corrosion test that could be performed using a corrosion-test system in accordance with an embodiment of the present disclosure.
Figure 5:
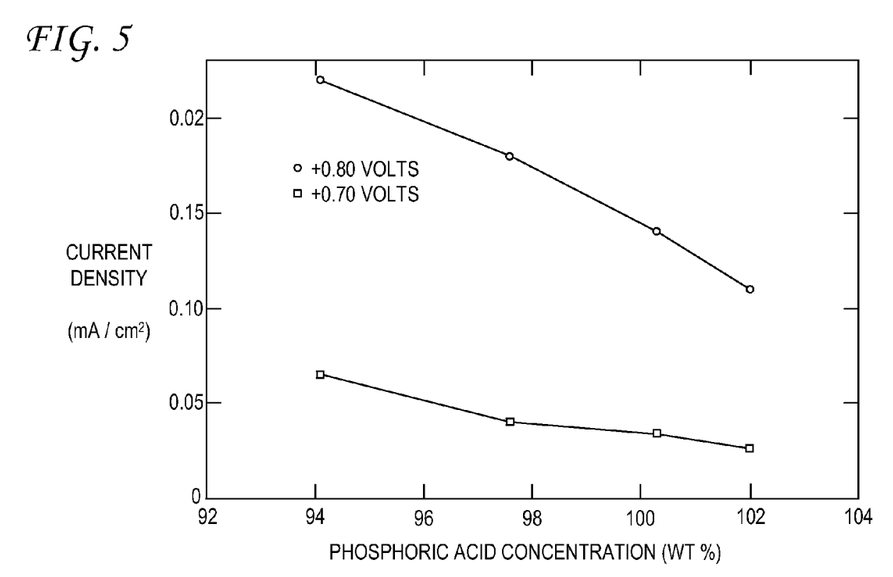
Figure 6:
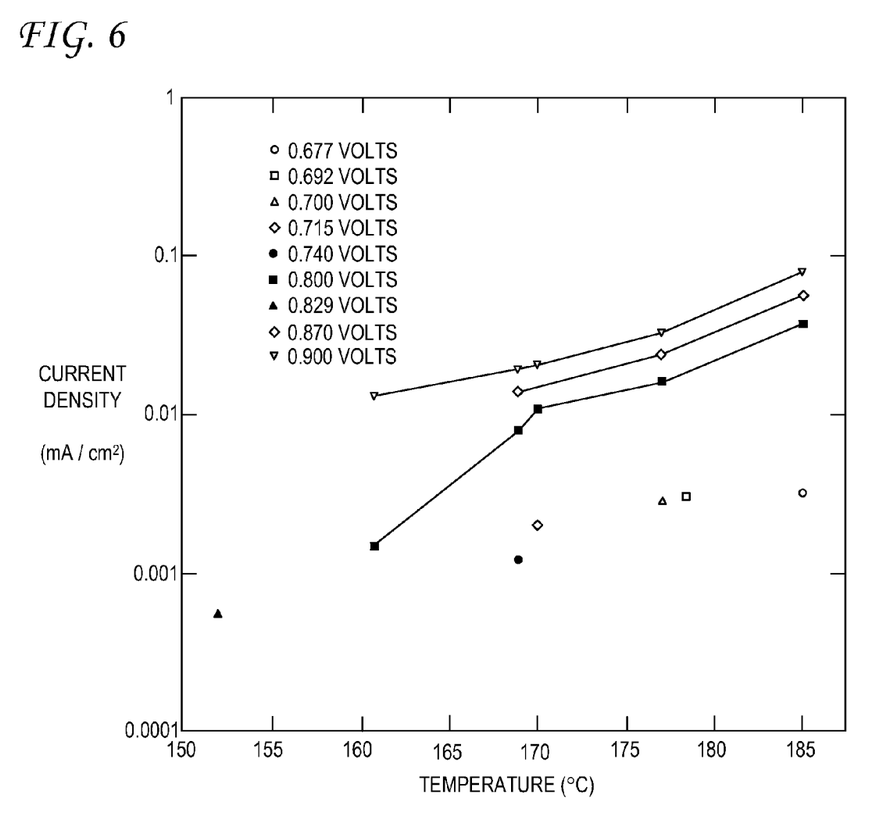

FIGS. 4-6 show graphs illustrating example results of a corrosion test that could be performed using corrosion-test system 26. In FIG. 4, current density is plotted on the vertical axis, and potential relative to the hydrogen reference electrode 60 is plotted on the horizontal axis. The graph includes seven plots, corresponding to data acquired at seven different temperatures in an electrolyte comprising phosphoric acid at the same concentration. In FIG. 5, current density is plotted on the vertical axis, and phosphoroic acid concentration is plotted on the horizontal axis. The graph includes two plots, corresponding to data acquired at the same temperature at two different potentials versus the hydrogen reference electrode. In FIG. 6, current density is plotted on the vertical axis, and temperature is plotted on the horizontal axis. The graph includes nine plots, corresponding to data acquired at nine different potentials applied to the specimen.

In other experiments, electrochemical data as shown in these figures could be acquired for multiple specimens tested together, in the same electrolyte. Such data could allow side-by-side comparison of differently constituted separator-plate materials in terms of their corrosion properties.

The configurations illustrated above enable various methods for conducting a corrosion test on a specimen immersed in an electrolyte in an electrochemical cell. Accordingly, some such methods are now described, by way of example, with continued reference to above configurations. It will be understood, however, that these methods, and others fully within the scope of the present disclosure, may be enabled via other configurations as well.

Figure 7:
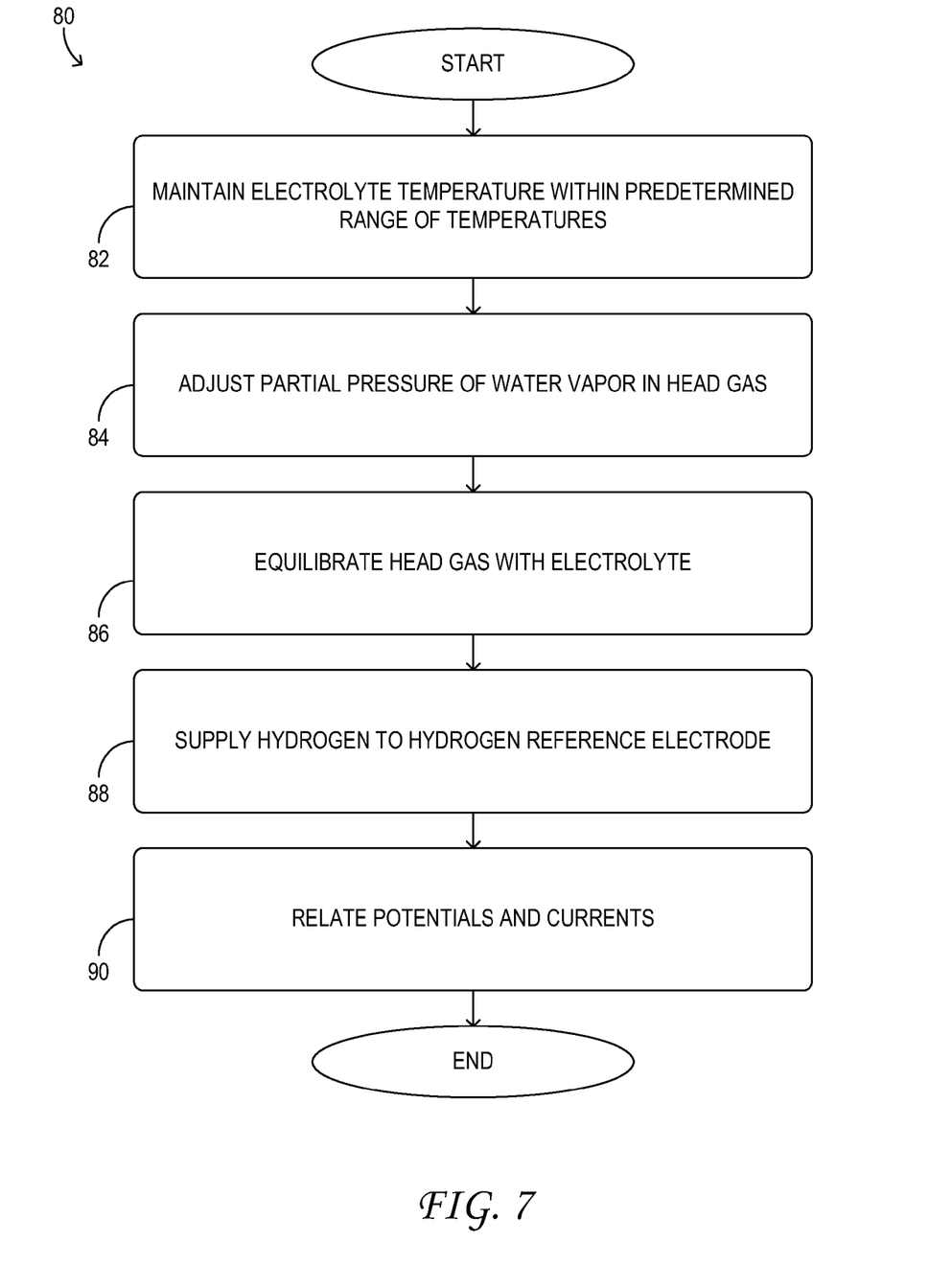
FIG. 7 illustrates a method for conducting a corrosion test on a specimen in one example embodiment in accordance with the present disclosure.

FIG. 7 illustrates a method 80 for conducting a corrosion test on a specimen in one example embodiment. The illustrated method may be conducted using a corrosion-test system such as corrosion-test system 26, for example, where the specimen is immersed in an electrolyte confined to an electrochemical cell, and where a head gas is confined over the electrolyte.

Method 80 begins at 82, where the temperature of the electrolyte is brought to and maintained within a predetermined range of temperatures. The predetermined range of temperatures may correspond to the range of temperatures experienced by a fuel cell installed in a fuel cell stack. In other embodiments, the range of temperatures may be higher than those experienced by a normally operating fuel cell to enact an accelerated-aging test of the specimen.

Method 80 then advances to 84, where the partial pressure of water vapor in the head gas is adjusted. The partial pressure of the water vapor may be adjusted so that the concentration of water in the electrolyte, when equilibrated with the head gas, falls within a predetermined concentration range. In one embodiment, adjusting the partial pressure of the water vapor may comprise admitting a gas having controlled water-vapor content into the electrolysis cell.

Method 80 then advances to 86, where the head gas is equilibrated with the electrolyte. In one embodiment, the head gas may be equilibrated with the electrolyte by waiting a predetermined period of time, temporarily stirring the electrolyte, and/or bubbling a gas through the electrolyte. Such bubbling and/or stirring is discontinued prior to acquiring electrochemical data.

Method 80 then advances to 88, where hydrogen is supplied to a hydrogen reference electrode, such as hydrogen reference electrode 60. Hydrogen may be supplied to the hydrogen reference electrode in any suitable manner. In one embodiment, however, the hydrogen may be supplied substantially as described in the configurations hereinabove. In particular, a hydrogen-segregating tube may partly enclose the hydrogen reference electrode and may partly separate the electrolyte nearest the hydrogen reference electrode from a balance of the electrolyte in the electrochemical cell. The hydrogen-segregating tube may further enclose an electrolysis cathode, distinct from the hydrogen reference electrode, and biased against an electrolysis anode. The electrolysis anode may also be suspended in the electrolyte, and an oxygen-segregating tube may partly enclose the electrolysis anode and may partly separate the electrolyte nearest the oxygen-evolving electrolysis electrode from a balance of the electrolyte in the electrochemical cell. In one embodiment, a controlled-current or controlled-voltage power supply may be used to bias the electrolysis cathode against the electrolysis anode.

Method 80 then advances to 90, where a plurality of potentials of the specimen is related experimentally to a plurality of currents drawn through the specimen. In one embodiment, the potentials and currents may be related experimentally by applying the plurality of potentials to the specimen while measuring the plurality of currents. Thus, the plurality of potentials may be applied potentiostatically to the specimen. In another embodiment, the potentials and currents may be related experimentally by drawing the plurality of currents through the specimen while measuring the plurality of potentials. By experimentally relating the potentials to the currents, an electrochemical property of the specimen—e.g., a potential-dependent corrosion property—may be measured. In these and other embodiments, the plurality of potentials may be referenced to the hydrogen reference electrode also immersed in the electrolyte.

It will be understood that some of the process steps described and/or illustrated herein may in some embodiments be omitted without departing from the scope of this disclosure. Likewise, the indicated sequence of the process steps may not always be required to achieve the intended results, but is provided for ease of illustration and description. One or more of the illustrated actions, functions, or operations may be performed repeatedly, depending on the particular strategy being used.

Finally, it will be understood that the articles, systems and methods described herein are exemplary in nature, and that these specific embodiments or examples are not to be considered in a limiting sense, because numerous variations are contemplated. Accordingly, the present disclosure includes all novel and non-obvious combinations and sub-combinations of the various systems and methods disclosed herein, as well as any and all equivalents thereof.

The invention claimed is:

1. A method for conducting a corrosion test on a specimen immersed in an electrolyte in an electrochemical cell, the method comprising:
   experimentally relating a plurality of potentials of the specimen to a plurality of currents drawn through the specimen by applying the plurality of potentials to the specimen while measuring the plurality of currents, or, by drawing the plurality of currents through the specimen while measuring the plurality of potentials; wherein the plurality of potentials are referenced to a hydrogen reference electrode also immersed in the electrolyte;
   supplying hydrogen to the hydrogen reference electrode via an electrolysis cathode distinct from the hydrogen reference electrode;
   measuring a corrosion property of a material from which the specimen is constructed based on the relating; and
   forming separator plates of a fuel cell, the separator plates including the material based on the measured corrosion property;
   wherein a first corrosion-resistant tube partly encloses the hydrogen reference electrode and partly separates the electrolyte nearest the hydrogen reference electrode from a balance of the electrolyte in the electrochemical cell.

2. The method of claim 1, wherein the first corrosion-resistant tube further encloses the electrolysis cathode.

3. The method of claim 1, wherein the electrolysis cathode is biased against an electrolysis anode also suspended in the electrolyte, wherein a second corrosion-resistant tube partly encloses the electrolysis anode and partly separates the electrolyte nearest the electrolysis anode from a balance of the electrolyte in the electrochemical cell.

4. The method of claim 3, further comprising biasing the electrolysis cathode against the electrolysis anode via a controlled-current or controlled-voltage power supply.

5. The method of claim 1, wherein the plurality of potentials are potentiostatically applied to the specimen, and wherein the corrosion property comprises corrosion resistance.

6. A method for conducting a corrosion test on a specimen immersed in an electrolyte in an electrochemical cell, the electrochemical cell also including a head gas disposed over the electrolyte, the method comprising:
adjusting a partial pressure of water vapor in the head gas so that a concentration of water in the electrolyte, when equilibrated with the head gas, will fall within a predetermined concentration range;
equilibrating the head gas with electrolyte; and
measuring an electrochemical property of the specimen.

7. The method of claim 6, wherein measuring the electrochemical property of the specimen comprises experimentally relating a plurality of potentials of the specimen to a plurality of currents drawn through the specimen, and includes one or more of applying the plurality of potentials to the specimen while measuring the plurality of currents, and, drawing the plurality of currents through the specimen while measuring the plurality of potentials.

8. The method of claim 7, wherein the plurality of potentials are referenced to a hydrogen reference electrode also immersed in the electrolyte, the method further comprising supplying hydrogen to the hydrogen reference electrode.

9. The method of claim 8, wherein a first corrosion-resistant tube partly encloses the hydrogen reference electrode and partly separates the electrolyte nearest the hydrogen reference electrode from a balance of the electrolyte in the electrochemical cell.

10. The method of claim 9, wherein the first corrosion-resistant tube further encloses an electrolysis cathode.

11. The method of claim 10, wherein the electrolysis cathode is biased against an electrolysis anode also suspended in the electrolyte, wherein a second corrosion-resistant tube partly encloses the electrolysis anode and partly separates the electrolyte nearest the electrolysis anode from a balance of the electrolyte in the electrochemical cell.

12. The method of claim 11, further comprising biasing the electrolysis cathode against the electrolysis anode via a controlled-current or controlled-voltage power supply.

13. The method of claim 8, wherein the plurality of potentials are potentiostatically applied to the specimen.

14. The method of claim 6, wherein equilibrating the head gas with the electrolyte comprises stirring the electrolyte.

15. The method of claim 6, wherein equilibrating the head gas with the electrolyte comprises bubbling a gas through the electrolyte.

16. The method of claim 6, wherein adjusting the partial pressure of water vapor comprises admitting a gas having controlled water-vapor content into the electrochemical cell.

17. The method of claim 6, further comprising maintaining a temperature of the electrolyte within a predetermined range of temperatures.

* * * * *